(12) United States Patent  
Stitzlein

(10) Patent No.: US 10,458,963 B2  
(45) Date of Patent: Oct. 29, 2019

(54) QUANTITATIVE HPTLC CANNABINOID FIELD TESTING DEVICE AND METHOD

(71) Applicant: Kathleen Stitzlein, Millersburg, OH (US)

(72) Inventor: Kathleen Stitzlein, Millersburg, OH (US)

( * ) Notice: Subject to any disclaimer, the term of this patent is extended or adjusted under 35 U.S.C. 154(b) by 0 days.

(21) Appl. No.: 15/617,798

(22) Filed: Jun. 8, 2017

(65) Prior Publication Data

US 2018/0292369 A1  Oct. 11, 2018

Related U.S. Application Data

(60) Provisional application No. 62/347,227, filed on Jun. 8, 2016.

(51) Int. Cl.  
*G01N 30/95* (2006.01)  
*G01N 30/94* (2006.01)

(52) U.S. Cl.  
CPC ............. *G01N 30/95* (2013.01); *G01N 30/94* (2013.01)

(58) Field of Classification Search  
CPC ............................... G01N 30/95; G01N 30/94  
See application file for complete search history.

(56) References Cited

U.S. PATENT DOCUMENTS

| | | | |
|---|---|---|---|
| 3,649,650 A | 3/1972 | Razdan et al. | |
| 3,766,884 A * | 10/1973 | Rosenthal | G01N 30/91 118/58 |
| 4,761,381 A | 8/1988 | Blatt et al. | |
| 4,829,010 A | 5/1989 | Chang | |
| 6,096,205 A * | 8/2000 | Haas | G01N 30/90 210/198.3 |
| 6,228,658 B1 | 5/2001 | Formica et al. | |
| 6,303,029 B1 * | 10/2001 | Nurok | G01N 30/90 204/600 |
| 6,937,330 B2 | 8/2005 | Dietz et al. | |
| 7,465,586 B2 | 12/2008 | Day et al. | |
| 7,790,400 B2 | 9/2010 | Jehanli et al. | |
| 7,816,143 B2 | 10/2010 | Day et al. | |
| 7,888,130 B2 | 2/2011 | Wuske et al. | |

(Continued)

FOREIGN PATENT DOCUMENTS

EP 0276732 1/1988  
WO 2012154306 11/2012

OTHER PUBLICATIONS www.CAMAG.com, "Instrumental Thin-Layer Chromatography 2013/14" accessed on archive.org snapshot on Aug. 19, 2014, pp. 5-18. (Year: 2014).*

(Continued)

*Primary Examiner* — Dennis White  
(74) *Attorney, Agent, or Firm* — Dominic A. Frisina

(57) ABSTRACT

A field testing device is provided for quantitating psychoactive components of marijuana such as THC in biological fluids such as saliva. Such a device may include an HPTLC plate for separating interferents from THC and may also include fluorometric components for quantitating THC. The device may include a microprocessor adapted to relate fluorescent intensity to analyte concentration through one or more calibration curves. Devices may optionally include microfluidics for carrying out HPTLC on biological samples including sample reservoirs, reagent reservoirs, micropumps, mixers, and the like.

20 Claims, 7 Drawing Sheets

(56) References Cited

U.S. PATENT DOCUMENTS

| 7,977,107 B2 | 7/2011 | Day et al. |
| 2014/0094391 A1 | 4/2014 | McDevitt et al. |

OTHER PUBLICATIONS

Jekaterina Mazina, A rapid capillary electrophoresis method with LEDinduced native fluorescence detection for the analysis of cannabinoids in oral fluid, Royal Society of Chemistry, Jul. 23, 2015, 7741-7747, The Royal Society of Chemistry.

* cited by examiner

QUANTITATIVE HPTLC CANNABINOID FIELD TESTING DEVICE AND METHOD

This application hereby incorporates U.S. Application No. 62/347,227 by reference in its entirety.

I. BACKGROUND OF THE INVENTION

A. Field of Invention

Embodiments may relate to point of care (POC) devices for quantifying psychoactive constituents of marijuana, and/or metabolites thereof, in vivo.

B. Description of the Related Art

The "green rush" is sweeping our nation with more than 20 states approving marijuana for medicinal use and other states such as Colorado, Oregon, Alaska and Washington having recreational and medicinal use laws in place. Lawmakers are working to establish standards for impairment in drugged drivers. These standards are also being used as guidelines for employers and insurance companies ranging from 2 ng/ml to 20 ng/ml in blood. Much attention has been given to oral fluid or saliva as a test medium for a variety of important physiological markers including those indicating marijuana use. Factors suggesting the desirability of oral fluid as a sample matrix include its suitability for collection in the field including at the road-side and work or school environments. Oral fluid collection is non-invasive and sample collection is inexpensive and simple. Since sample collection can be witnessed, oral fluid is also difficult to adulterate or substitute.

More importantly oral fluid has been determined to be a reliable indicator of *cannabis* use. Research indicates that the $\Delta^9$-tetrahydrocannabinol (THC) levels found in the oral fluid of drug users closely reflect levels found in the blood. Moreover, oral fluid can provide analytically useful samples over a window from very recent use to up to 14 hours after use. It has further been shown that the amount of THC found in oral fluid corresponds to the length of time the drug remains active in the body. The concentration of THC in oral fluid is proportional to the concentration found in plasma or blood and it contains predominately the parent drug as opposed to the metabolites.

Currently, quantitative THC testing is performed in laboratory settings using methods such as gas chromatography-mass spectrometry, thin layer chromatography followed by densitometry, radioimmunoassay and continuous flow immunoassay. These methods provide very sensitive and accurate results but are unsuitable for use in the field. More specifically, the chromatographic methods being used to isolate cannabinoids include gas chromatography (GC), high pressure liquid chromatography (HPLC) and high performance thin layer chromatography (HPTLC) along with some other variations of these techniques. Of these methods gas chromatography-mass spectrometry (GS-MS) is considered the gold standard for confirmatory quantification for THC.

The four main immunoassay techniques currently being used are enzyme-linked immunoassay (ELISA), fluorescence polarization immunoassay (FPIA), enzyme multiplied immunoassay technique (EMIT) and radioimmunoassay (RIA). All of these immunoassay methods are very sensitive and can be applied directly to the samples being tested, however; the major problem with these techniques is one of selectivity. The cannabinoids are a large group of closely related compounds and cross-reactivity between the different molecules leads to a high rate of false positives. Results from testing involving immunoassay must be followed up by a chromatographic method for confirmation.

One of the major problems with laboratory testing is that the results of these tests often take weeks to months to process and the equipment required is expensive and unsuitable for use outside of the lab. There are no commercially available quantitative point of care devices being used for roadside or mobile testing for THC.

In states where marijuana use is legal, if a driver is suspected of drugged driving they must be taken to a local hospital or lab by ambulance for testing and their car may be impounded. This process can take up to several hours sometimes resulting in a drop in THC levels by the time testing occurs. In some states, such as Ohio, a search warrant issued by a judge is required before a blood draw is allowed. The decision to test a driver must be made at the roadside with no objective method to indicate whether or not to incur the expense and inconvenience of testing. If a driver is convicted of drugged driving the expense is covered by DUI fines but if they are below the legal limit then the state must pay for the cost of testing and transporting the driver. If it is difficult for lawmakers and law enforcement officers to know how much THC is in the system of the average user, it is impossible for the user to measure their own levels to empower them to make informed decisions about their ability to drive safely. This is an urgent problem that is currently affecting people from all walks of life.

There are a number of point of care qualitative test methods already on the market which provide fast positive or negative detection for various drugs of abuse including cannabinoids. Most of these products involve the testing of urine for metabolites of THC indicating marijuana use. The problem with these products is that the results have little connection to current impairment levels. Many cannabinoid molecules including THC are fat soluble with very low solubility in water and can therefore be found in the body for up to 30 days or more after use. These products are not suitable for establishing impairment in states that have legalized marijuana use or in states such as Ohio that have established impairment levels for prosecution.

There are also products on the market using saliva as a test medium for cannabinoids such as The DrugCheck SalivaScan, Accu-Tell Rapid Cannabinoids Saliva Test, Drug-Wipe®, Cozart®, RapidScan, Rapid Stat®, Oratec XP, and the Drager Drug Test 5000®. The Dräger Drug Test 5000 is currently being used in Australia as a method of roadside testing for impaired drivers. These products are all immunoassay-based devices which are designed only to screen for the presence of cannabinoids, not the level, and all have problems with accuracy and precision. The main drawbacks reported include false positives due to cross-reactivity between cannabinoids and other interferents, false negatives, poor analyte recovery and inadequate performance.

Two of the main cannabinoids found in oral fluid are THC, and CBD. The ability to separate these two very closely related cannabinoids is a critical requirement of any POC testing for intoxication. While THC potency is valued for its intoxicating effects, CBD is not considered psychoactive and is a cannabinoid of intense interest for medicinal purposes. Studies evaluating current test products for detecting drug use have higher error rates in results obtained for non-laboratory personnel. This highlights the need for the design of a system which is simple to use, requiring few operator steps to obtain repeatable results.

Laboratory testing gives accurate and sensitive quantitative results, but these methods are expensive, time consuming and unsuitable for use at the roadside. Tests providing qualitative or semi-quantitative results, especially those testing for *cannabis* metabolites, may not be good indicators of current impairment levels. The emerging breathalyzer technologies have many obstacles to overcome and may not be capable of providing quantitative results. Some embodiments of the present invention may provide one or more benefits or advantages over the prior art.

Some embodiments of the present invention may provide one or more benefits or advantages over the prior art.

II. SUMMARY OF THE INVENTION

Some embodiments may relate to an analytical cartridge, comprising: a sample receptacle adapted to receive a volume of liquid sample; a pump having an intake in fluid communication with the sample receptacle; a development chamber adapted to contain a thin layer chromatography mobile phase; a stationary phase disposed within the development chamber and suitable for conducting thin layer chromatography; a sample deposit area of the stationary phase in fluid communication with an output of the pump; a mobile phase reservoir adapted to contain a thin layer chromatography mobile phase; and a casing combining, into the form of a cartridge, the sample receptacle, the pump, the development chamber, the stationary phase, the sample deposit area, and the mobile phase reservoir.

According to some embodiments the sample receptacle includes a mixer adapted to mix liquid samples contained therein.

Some embodiments may also include a cover for enclosing the development chamber.

According to some embodiments the cover is retractable, removable, and/or optically clear to light between 190 nm and 800 nm.

According to some embodiments the pump is a peristaltic pump.

According to some embodiments wherein the stationary phase, or an additive thereto, fluoresces in ultraviolet light.

According to some embodiments the mobile phase reservoir comprises a blister pack that is breakable to communicate mobile phase contained therein to the development chamber.

Some embodiments may also include a reagent reservoir in fluid communication with the a mixing chamber and/or the development chamber, the reagent reservoir being adapted to dispense a solvent, a buffer, a derivatizing agent, and/or an emission enhancing agent to the mixing chamber and/or the development chamber.

Embodiments may further relate to a cannabinoid quantitation device, comprising: a cartridge as described above; an excitation source emitting light suitable for measurably exciting electrons in a cannabinoid UV absorption band, the excitation source being in optical communication with a stationary phase of the cartridge; an emission detection component operatively sensitive to cannabinoid emission resulting from relaxation of the excited electrons, the emission detection component being in optical communication with the stationary phase of the cartridge; and a microprocessor adapted to receive spectral data collected by the emission detection component and calculate a cannabinoid concentration from predefined calibration curves.

According to some embodiments the excitation source comprises an ultraviolet light emitting diode having operably sufficient spectral output between 210 nm and 250 nm to quantitate the cannabinoid.

According to some embodiments the excitation source simultaneously illuminates all analyte spots on the stationary phase.

According to some embodiments the emission detection component is an image-forming device operably sensitive to light between 295 nm and 315 nm to quantitate the cannabinoid.

According to some embodiments light impinging the emission detection component is filtered to exclude light from the excitation source and pass light emitted by analytes.

According to some embodiments the excitation source serially illuminates analyte spots.

According to some embodiments the excitation source comprises an ultraviolet LED laser having operably sufficient spectral output between 210 nm and 250 nm to quantitate the cannabinoid.

According to some embodiments the excitation source comprises a non-laser collimated ultraviolet LED having operably sufficient spectral output between 210 nm and 250 nm to quantitate the cannabinoid.

Embodiments may also include a moveable mask adapted to expose analyte spots serially to light from a non-laser un-collimated ultraviolet LED having operably sufficient spectral output between 210 nm and 250 nm to quantitate the cannabinoid.

According to some embodiments the emission detection component is a non-image-forming device operably sensitive to light between 295 nm and 315 nm to quantitate the cannabinoid.

Embodiments may also include an imaging chamber adapted to exclude ambient light and adapted to support the cartridge, the excitation source, the emission detection component, and the microprocessor in an optically aligned relation to each other.

Other benefits and advantages will become apparent to those skilled in the art to which it pertains upon reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof, wherein like reference numerals indicate like structure, and wherein.

IV. DETAILED DESCRIPTION OF THE INVENTION

Figure 1A:
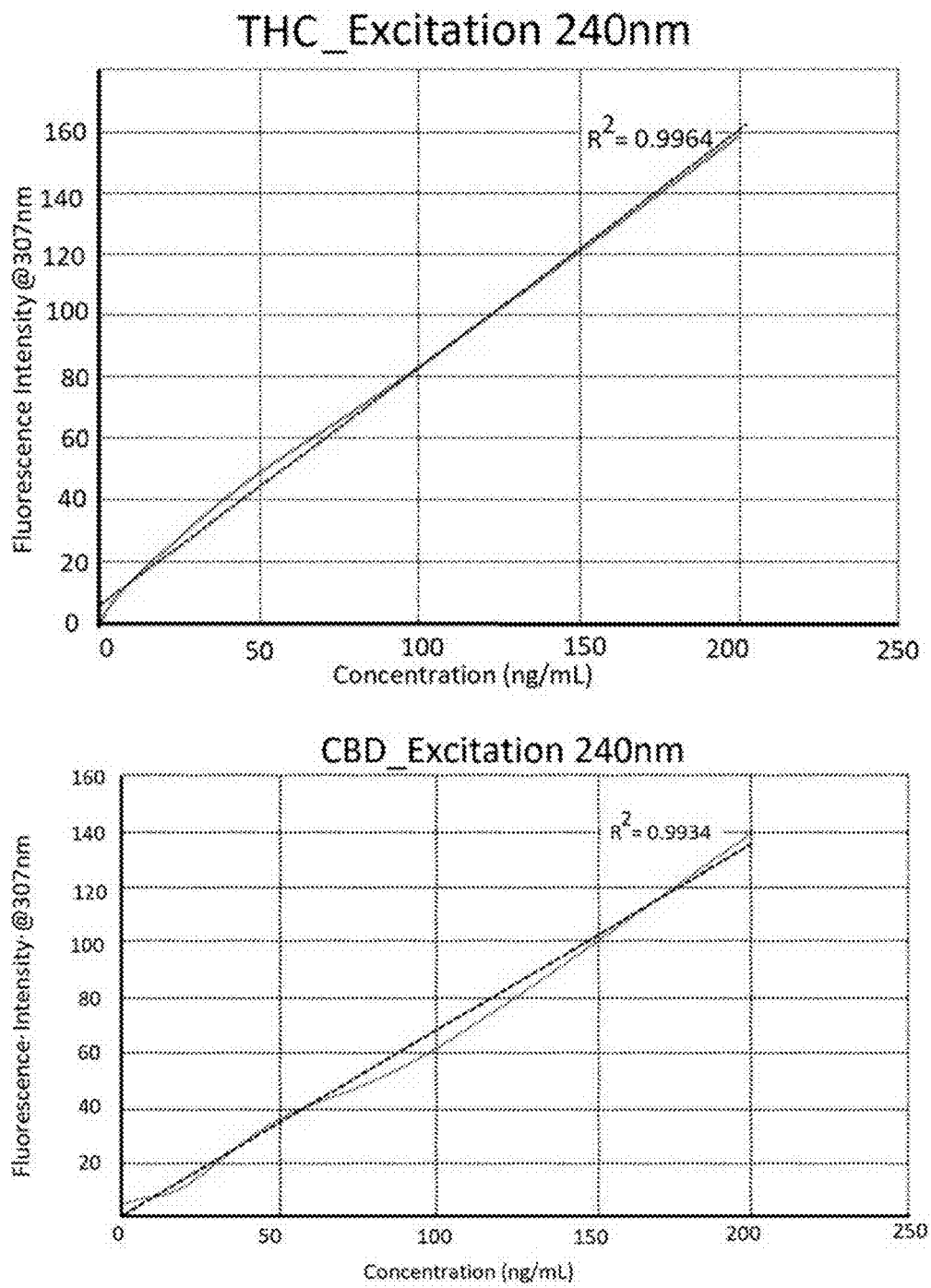
FIG. 1A is a pair of graphs illustrating the linearity of THC and CBD fluorescence with respect to concentration when excited at 240 nm.

All drawings and figures contained herein are for purposes of illustrating embodiments of the invention only and not for purposes of limiting the same.

Headings are used herein for convenience purposes only. Paragraphs under differing headings may include similar or even overlapping teachings. Accordingly, headings are not meant to limit the invention and should not be used to construe the meaning of teachings thereunder.

As used herein the terms "embodiment", "embodiments", "some embodiments", "other embodiments" and so on are not exclusive of one another. Except where there is an explicit statement to the contrary, all descriptions of the features and elements of the various embodiments disclosed herein may be combined in all operable combinations thereof.

Language used herein to describe process steps may include words such as "then" which suggest an order of operations; however, one skilled in the art will appreciate that the use of such terms is often a matter of convenience and does not necessarily limit the process being described to a particular order of steps.

Conjunctions and combinations of conjunctions (e.g. "and/or") are used herein when reciting elements and characteristics of embodiments; however, unless specifically stated to the contrary or required by context, "and", "or" and "and/or" are interchangeable and do not necessarily require every element of a list or only one element of a list to the exclusion of others.

Except where otherwise required by context, the word "may" and the phrase "may be" are used herein to indicate that a particular act or structure is within the scope of the present invention, is consistent with one or more elements of the invention, and/or supports patentability of the claimed invention. With particular regard to acts, statements indicating that an act "may be" performed are used herein to indicate that carrying out the act is expected to produce results supporting patentability of the invention claimed herein based on experimental data and/or the inventor's experience and expertise in the art. The word "may" and the phrase "may be" do not mean that the indicated act was actually carried out, nor should it be construed to suggest that the act was not carried out, or that the applicant is unsure whether the act or structure is or is not within the scope of the invention, or that the applicant is unsure whether the recited act or structure is permissible, possible, or practical.

Where the word fluorescent is used herein, its use is not meant to exclude phosphorescence or bioluminescence where phosphorescent or bioluminescent alternatives are available to the person having ordinary skill in the art. Such variations are contemplated to be within the scope of the present invention.

All solvents and chemicals are of analytical grade. Drug standards of $\Delta^9$-tetrahydrocannabinol (THC), CBD, CBN, and THC-COOH may be purchased from Cerilliant (Round Rock, Tex., USA). Cannabinoid solutions may be prepared in methanol and diluted to required concentrations. All drug compounds may be stored at −20° C. Saliva, urine, and blood from volunteer donors may be used to show viability of quantifying THC in bodily fluids. Comparison of results with certified reference standards may be used to assure the identity of the THC analyte. The potential interferents commonly found in oral fluid such as food particles, tobacco, caffeine and other drugs of abuse may be considered and included in test samples at appropriate levels during the validation procedure to assure that results are unaffected.

Calibration solutions may be prepared using certified reference solutions of THC, CBD, CBN and 11-nor-9-carboxy-Δ9-THC; each of 1 mg/mL in methanol, may be purchased from Cerilliant Corporation (USA). Individual calibration solutions of THC may be prepared and tested as well as solutions with mixtures of the other cannabinoids commonly found in oral fluid using methanol as the diluent. Fresh negative oral fluid samples spiked with purchased standards may be tested. Self-identified, declassified, drug-positive oral fluid samples from volunteers may be tested. Method validation may be performed with pure cannabinoid standards. Method performance was evaluated using spiked oral fluid as well as native drug-positive samples.

Sample preparation and pre-conditioning, is desirable or even necessary in some pre-existing analytical tests; however, embodiments of the present invention may use "raw" or "neat" oral fluid with little or no pre-purification or preparation. Proceeding without preparative steps may increase the speed of carrying out sample analyses, and may decrease the apparent complexity from the point of view of the user. However, embodiments may include preparative steps after the user introduces a sample. For instance, automated microfluidics may be preconfigured to carryout preparative steps that are unseen by the user.

Linearity of Cannabinoid Concentration Versus Florescent Intensity $\Delta^9$-Tetrahydrocannabinol (THC) and cannabidiol (CBD) are demonstrated to have a linear relationship between concentration and fluorescent intensity over an analytically useful range for quantifying intoxicating drug levels. Standard solutions of 1 mg/mL in methanol each may be purchased from Cerilliant Corporation (USA) and diluted to make calibration standards. The stock solutions may be stored at −20° C. Calibration solutions of 0, 5, 20, 50, 100 and 200 ng/mL may be prepared using methanol as the diluent. This range encompasses the current legal standards for intoxication (5 ng/mL-20 ng/mL). Fluorescence emission spectral measurements at an excitation range from of 230 nm to 400 nm may be taken three times with three replicates at each concentration using a Perkins Elmer LS50B Luminescence Spectrometer. Solutions may be mixed for 30 seconds before each measurement is taken to assure homogeneity. The results displayed in FIG. 1A illustrate liquid phase measurements of the fluorescence emission intensity versus sample concentration using an excitation of 240 nm. Standards may be spotted on an embodiment, dried, and then measured according to fluorescent methods described herein to establish a calibration curve for quantitating THC or other compounds of interest.

The data shown in FIG. 1A illustrates that fluorescence may be used to measure the concentration of THC and CBD in solution with acceptable linearity and sensitivity in concentration ranges suitable for assessing intoxication, i.e. 5-100 ng/mL. Furthermore, the data illustrate that an off-peak excitation of 240 nm, as opposed to 230 nm (on-peak), can be used as the excitation frequency, which permits the use of a commercially available and relatively low-cost UV-LED source.

Measurements similar to those shown in FIG. 1A may be made using oral fluid rather than methanol. Oral fluid was shown to have a matrix effect caused by light scattering. Thus, liquid phase fluorescence measurements of such analytical samples require a correction factor that is expected to vary from one oral fluid to another. However, no such correction factor is necessary for measurements made with embodiments of the invention comprising TLC separation devices and methods.

Figure 1B:
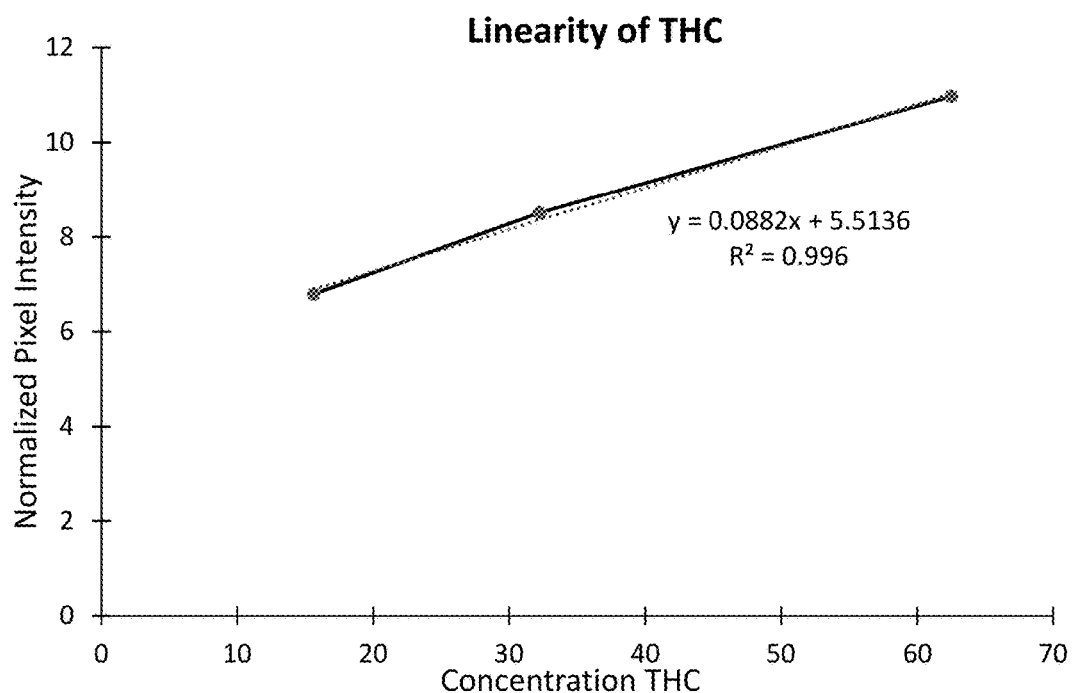
FIG. 1B is a graph showing the linearity of HPTLC/Fluorescence measurements according to an embodiment of the invention.

FIG. 1B illustrates the linearity of detection and measurement methods of the invention. Particularly, THC concentration in oral fluid is determined by HPTLC in combination with fluorescence intensity measurements. Excitation wavelength was 366 nm. The HPTLC method is linear between 0.2 ng/spot and 30 ng/spot. This range includes THC concentrations expected in oral fluid after smoking marijuana.

Figure 1C:
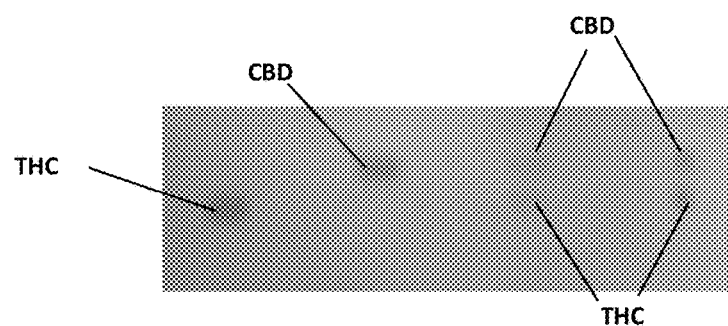
FIG. 1C is a photograph of an HPTLC plate illustrating an embodiment's capacity to separate an important interferent from THC.

FIG. 1C is a photograph of an HPTLC plate illustrating adequate separation of THC and CBD according to methods of the invention taught herein. The plate is visualized with an aqueous solution of 0.1% 4-Benzoylamino-2,5-dimethoxyaniline, Azoic Diazo No. 24. THC and CBD standards are shown having been run against mixtures of CBD and THC.

Chromatography

It is demonstrated that HPTLC is useful for quantitating THC in mixtures of THC and CBD. Samples and standards may be spotted on at least three types of commercially available plates: Si60 HPTLC glass plates, Si60 HPTLC glass plates coated with fluorescent indicator F254, Si60 UTLC glass plates, and C-18 HPTLC plates coated with fluorescent indicator F254. Application of 5 µL samples to the plates may be carried out using a capillary liquid dispensing system such as, and without limitation, CAMAG Nanomat 4. Advantageously, samples may be applied 1 cm from the bottom of the plate and 2 cm from the sides. Sample volumes of 100 µL to 400 µL may be used to increase the concentration of cannabinoids available for spot detection leading to increased sensitivity.

Plates may be developed in a twin trough chamber and/or a horizontal development chamber such as, and without limitation, CAMAG Horizontal Developing Chamber 2, without vapor saturation or humidity control. The developing solvent used for normal phase plates is heptane/diethyl ether/formic acid (or acetic acid); 75/25/3 drops, v/v/v. The developing solvent for reverse phase plates is methanol/DI water; 80/20, v/v. The developing distance for the normal phase plates is 5 cm from the spot application position and which occurs in approximately eight minutes. The developing distance for the reverse phase plates is 3.5 cm and occurs in approximately four minutes. Results such as these are consistent with environmental conditions in the lab of around 16-17° C. and relative humidity <50%. The person having ordinary skill in the art will readily understand that a variety of solvent systems humidity and temperature conditions may be suitable and it would be within the skill of the art to make such a selection.

The developed plates are dried with a stream of warm air for approximately three minutes to remove residual solvents. See Table 1 for various derivatizing reagents and conditions used to enhance fluorescence. Results are observed under UV 254, UV 366 and visual light.

TABLE 1

TLC Experiment Conditions for Derivatization Reagents for Enhanced Visualization.

| Sample Tested | Derivatization Regent | Preparation, use |
|---|---|---|
| 1 mg/mL THC in Methanol | Diphenylboric Acid 2-Amino Ethyl Ester | Dipping & dry for 5 min. with hair dryer |
| 1 mg/mL THC in Methanol | Polyethylene Glycol 400 | Dipping & dry for 5 min. with hair dryer |
| 1 mg/mL ea. THC, CBD, CBN, THC-COOH in Methanol-concentration of 100 µg/mL | Fast Blue Salt | Dipping & dry for 5 min. with hair dryer |

Enhancing Sensitivity

Derivatizing THC and THC-COOH with dansyl chloride (5 Dimethylamino-naphthanlene-1-sulphonyl Chloride) enhances their fluorescent quantum yield and thus leads to improved sensitivity and limits of detection. Dansylation of samples may be achieved by adding 100 µL NaOH to 1 mL of test fluid to adjust the sample pH to 10+ followed by adding 1 mg/mL of dansyl chloride solution (1 mg/mL in acetone). The samples may be heated for approximately three minutes at 60° C. and cooled at room temperature. Derivatized samples may be applied according to procedures disclosed herein for non-derivatized samples.

Device

A device for the roadside quantitation of THC in oral fluid or other bodily fluids may include HPTLC components to separate and isolate cannabinoids, and may include fluorescence detection components to measure the native fluorescence or enhanced fluorescence (e.g. dansylated, derivatized, or conjugated) of THC and/or THC derivatives.

Embodiments of the invention may comprise a device adapted to quantitatively identify psychoactive cannabinoids and/or metabolites thereof in biological samples including, without limitation, human oral fluid and plant tissue preparations. Devices according to embodiments of the invention may include a cartridge adapted to support a stationary phase suitable for thin layer chromatography (TLC), and may include microfluidics adapted to apply analytical samples to the stationary phase and contact the stationary phase with a suitable mobile phase. Cartridges according to some embodiments may include adaptations capable of receiving biological fluid samples, and/or contacting the biological fluid samples with analytical sample deposit areas of the stationary phase. Moreover, cartridges according embodiments of the invention may be adapted to cooperate with optical components thereof to fluorometrically quantitate analyte concentrations, e.g. in oral fluid.

Biological samples such as oral fluid may be introduced or applied to an embodiment without dilution or preparation, i.e. neat. However, diluting samples and/or adding reagents to samples may also be compatible with embodiments of the invention. Diluted samples may include buffers such as, without limitation, phosphate buffered saline (PBS) or physiological saline, or may include solvents such as, without limitation, methanol or water. Reagents may include one or more of derivatizing agents, luminescent tags or markers including luminescent and phosphorescent chemical species, antigens, bioluminescent chemical species, catalysts, enzymes, substrates, and the like. Moreover, reagents may include solid phase reagents as well as liquid phase reagents. Embodiments may include one or more reservoirs and microfluidic components for introducing diluents to a sample and/or mixing diluents into a sample.

Cannabinoids are known to have absorption peaks around 210-250 nm, and some particularly useful cannabinoids, including Δ9-tetrahydrocannabinal (THC) and cannabidiolic acid (CBD), have absorptions peaks between 220-240 nm with useful absorption bands up to 400 nm. More specifically, a particularly advantageous absorption peak is 230 nm with a corresponding emission peak wavelength of 305 nm. The skilled artisan will appreciate that the specific wavelength may shift by a few nm according to experimental conditions including solvent effects, pH, and temperature.

In view of the known absorption characteristics of cannabinoids, embodiments may include an appropriate ultraviolet source to excite cannabinoids, and a suitable optical arrangement may be applied to detect native fluorescent emission of cannabinoids which is known to occur around 305 nm. Embodiments may employ one of several optical arrangements including detecting emission at 90 degrees relative to the emission source using filters to remove excitation radiation while passing emission radiation, and using various photosensitive detectors to quantify emission signals. As used herein, detection at 90 degrees may include front-face detection modes including without limitation where the emitter and detector are 90 degrees from each other, but each is 45 degrees from the front face of the sample. Such a front face detection mode may be particularly advantageous for taking spectral measurements of TLC spots. Embodiments may also include structures for detecting emission in transmission mode, e.g. at 180 degrees relative to the emission source.

With regard to determining the degree of current intoxication by quantitating cannabinoids, oral fluid has been found to be particularly useful. Notably, both THC and CBD are found in oral fluid, but only THC is psychoactive. Since THC and CBD have overlapping absorption and emission spectra, these compounds must be spatially separated in order to accurately quantitate THC. Spatial separation is achieved by embodiments of the invention through thin layer chromatographic features and adaptations.

Embodiments of the invention may also find application in grading the potency of marijuana by quantifying the amount of psychoactive components in plant tissues. According to such applications, plant tissue may be sampled from a marijuana plant and THC and/or other psychoactive compounds may be extracted from the tissue according to known methods. For example, and without limitation, plant tissue samples may be extracted with solvents such as ethanol, methanol, tetrahydrofuran (THF), naphtha, petroleum ether; or edible oils such as olive oil, coconut oil, or canola oil. Other known extraction methodologies use carbon dioxide, or volatile hydrocarbons such as butane or propane. Plant tissues may be extracted as-sampled or may prepared for extraction through known mastication or homogenization methods. The plant extract derived according to these methods may be spotted on a stationary phase of an embodiment with or without dilution depending on concentration. Highly concentrated samples may require dilution in order to prevent streaking on the TLC plate and/or to obtain linear measurements of concentration.

Figure 2A:
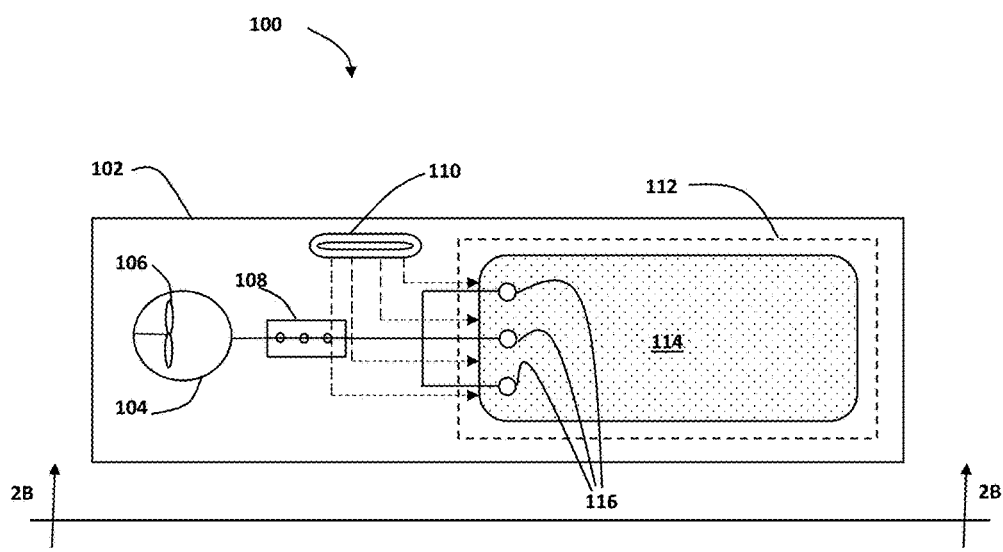
FIG. 2A is a plan view of a lab-on-chip microfluidic device according to one embodiment of the invention.

FIG. 2A is a plan view diagram of a cartridge 100 according to one embodiment. The cartridge 100 includes a casing or enclosure 102 adapted to contain and/or comprise various fluidic and analytical adaptations. One such adaptation is a sample receptacle 104 adapted to receive a sample fluid such as oral fluid or plant extract. The sample receptacle 104 of this embodiment optionally includes a mixer 106. The receptacle 104 is in fluid communication with a peristaltic micropump 108 which is adapted to draw fluid from the sample receptacle 104 and distribute it to a plurality of analytical sample deposit areas 116 of a TLC stationary phase 114. The stationary phase 114 is disposed within a development chamber 112 which is in fluid communication with a mobile phase reservoir 110.

According to the embodiment shown in FIG. 2A, a sample fluid sample may be deposited in the receptacle 104 and a predetermined volume of the sample may be delivered to each of the plurality of analytical sample deposit areas 116. The mobile phase may then be released from the reservoir 110 and development may be allowed to proceed for a predetermined amount of time. The TLC plate may then be dried thus stopping separation, and fixing the analytes in place on the plate. The analytes may then be quantitated using spectroscopic methods of the invention.

Figure 2B:
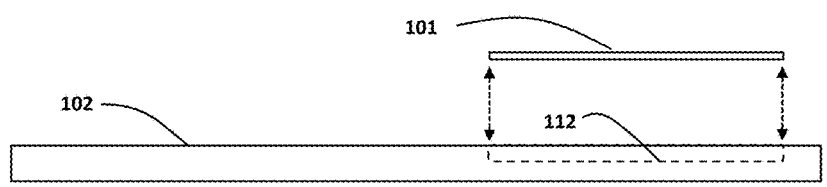
FIG. 2B is a side cross sectional view of the device shown in FIG. 2A taken along line 2B-2B.

FIG. 2B is a side view of the cartridge 100 taken along line 2B-2B, which is intended to illustrate that the components of this embodiment are contained within the casing 102, or are recessed. For instance, the TLC stationary phase 114 must optically communicate with components external to the cartridge 100 and thus cannot be enclosed within opaque walls; however, it may be advantageous to protect the stationary phase 114 from abrasion. Therefore, one suitable arrangement may include a recessed cavity containing the stationary phase 114. The recessed cavity may optionally include a cover 101 that may be retractable, removable, or optically clear to UV-Vis spectrum light. The cover may serve to retain solvent vapors during development, but permit optical communication during quantitation. It may be desirable to have a retractable or removable cover so that solvent and/or solvent vapors can be vented quickly to stop the separation at a well-defined predetermined time.

Figure 3:
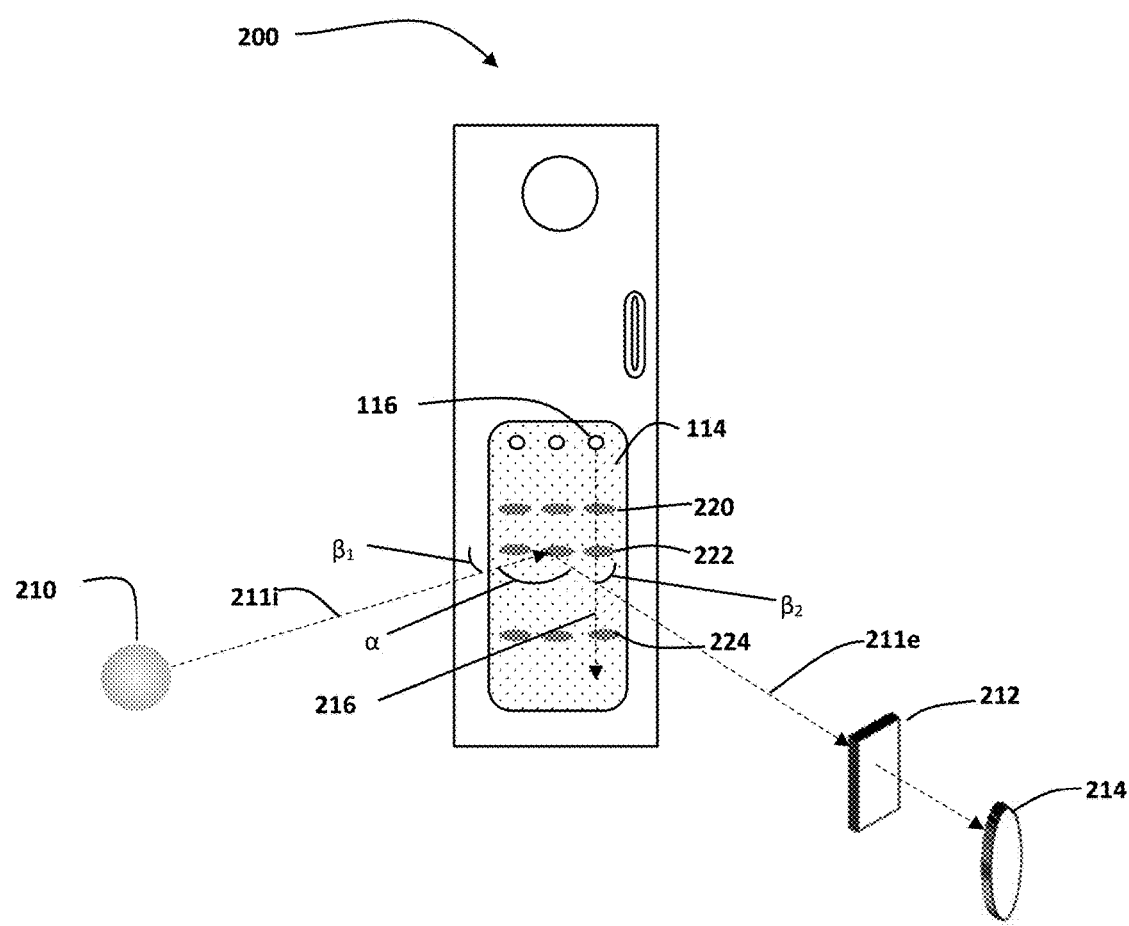
FIG. 3 illustrates an embodiment separating fluorescent analytes by high performance thin layer chromatography (HPTLC) while showing the relative positions of an excitation light source and detector-side optics including a long-pass filter.

FIG. 3 illustrates an embodiment 200 that includes optical elements external to the cartridge 100 where a light source 210, long-pass filter 212 and detector 214 lie on an optical path forming a front-face detection arrangement. Arc $\beta_1$ illustrated in FIG. 3 corresponds to the angle between the face of face 100 and an incident ray 211$i$ from the light source 210. Arc $\beta_2$ illustrated in FIG. 3 corresponds to the angle between the face of cartridge 100 and an emitted ray 211$e$ traveling along a line of sight of the detector 214. Arc $\alpha$ corresponds to the angle between the light source 210 and the detector 214 as defined by the incident ray 211$i$ and the emitted ray 211$e$. The particular values of $\beta_1$, $\beta_2$, and $\alpha$ are non-critical however for embodiments may include setting $\alpha$ to 90 degrees and setting both $\beta_1$ and $\beta_2$ to 45 degrees.

The cartridge 100 of the embodiment 200 includes three deposit areas 116 forming three lanes 216 so that samples may be run in triplicate. One skilled in the art will appreciate that the embodiment 200 would be enclosed so as to exclude ambient light, and that the detector 214 would be isolated from the light source 210 so that it only receives filtered light. Enclosures and optical isolation structures are omitted from FIG. 3 to more clearly show the relative position of the cartridge 100 and external optical components 210, 212, and 214; however, the skilled artisan will readily appreciate how such structures can be fashioned and incorporated without undue experimentation.

The light source 210 of FIG. 3 may emit at a wavelength coinciding with the absorption (i.e. excitation) bands of the various analytes. Light sources may include, for instance and without limitation, an ultraviolet light emitting diode (UV LED) having an emission peak at 240 nm, or otherwise having analytically useful emission intensity in the 230 nm to 240 nm wavelength range. Depending on the nature of the detector 214, the source 210 may illuminate all of the analyte spots at once, or it may illuminate them one at a time. More specifically, if the detector 214 is a charge coupled device (CCD), or other image-forming device such as a mobile phone camera, then the light source 210 can illuminate the entire stationary phase 114 at once. The CCD detector or other camera can be relied upon to relate light signals to particular analyte spots.

However, if the detector 214 is a photodiode or other non-image-forming light detection device then the light source 210 may illuminate one spot at a time so that the detected light may be attributed to a particular spot. Illumination of one analyte spot at a time may be accomplished with focusing and/or collimating optics, by using a UV diode laser as source 210, or by interposing a movable mask between the source 210 and the stationary phase 114. Furthermore, the photodiode detector may optionally include a long-pass filter 212 as an optical layer deposited on the photodiode.

With continuing regard to FIG. 3, the sample spots 220, 222, and 224 may emit at characteristic wavelengths, or the same wavelength, and a portion of the emission may pass through long-pass filter 212 which may remove excitation radiation from the optical path. The brightness of the spots 220, 222, and 224 is directly proportional to the amount of analyte present, and is thus relatable to the concentration of analyte in the original sample. A suitable filter may be used to remove light originating from the light source 210 while passing the cannabinoid emission peak. For instance and without limitation, in the case of cannabinoid quantitation, the light source may have an emission peak around 240 nm, and the analyte may have an emission peak centered around 305 nm. The filter 212 may be free-standing, or the filter 212 may be deposited on the detector 214 as an optical layer according to known methods. Depositing the filter as an optical layer may eliminate the need for otherwise isolating the detector 214 from the light source 210.

Figure 4:
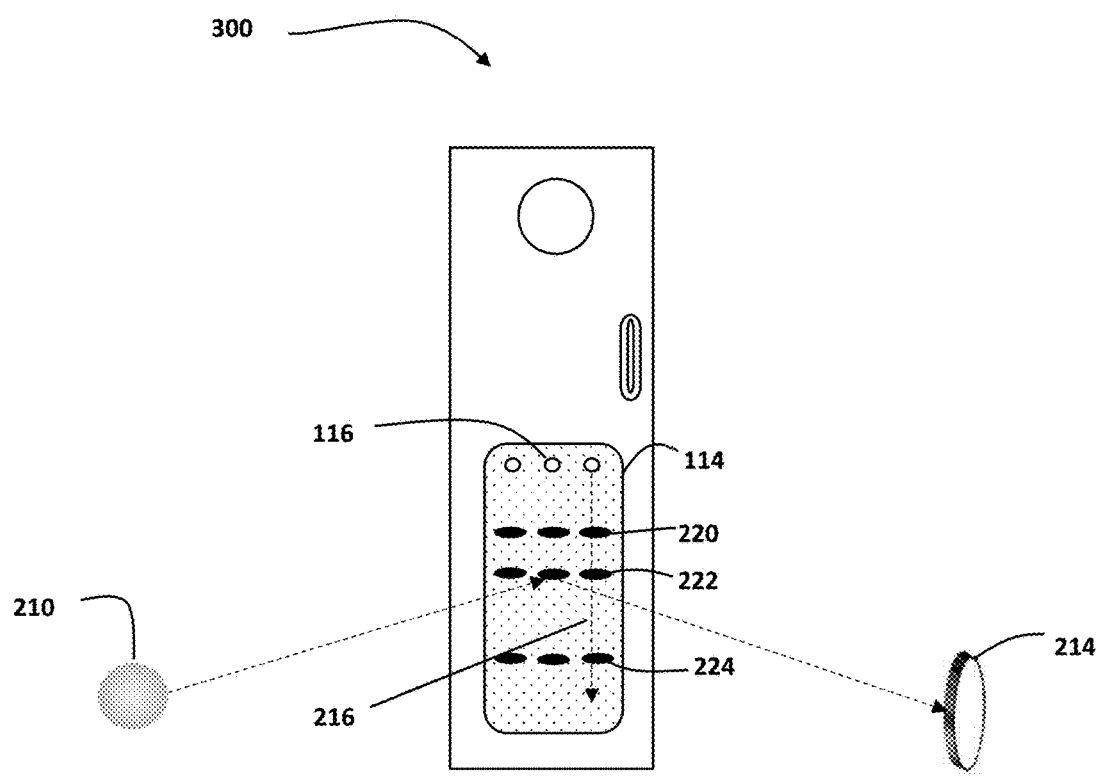
FIG. 4 illustrates an embodiment showing a fluorescent background embodiment where the analytes are either non-emitting or their emission can be neglected without the need for filter optics.

FIG. 4 illustrates an embodiment 300 where the native fluorescence of the analyte spots 220, 222, and 224 is neglected in favor of a fluorescent background. In this embodiment, the emission characteristics of the stationary phase itself, or of a compound bound to or otherwise impregnated into the stationary phase, are used to generate a fluorescent background. Advantageously, the background may absorb and/or emit at a wavelength different from that of the analyte spots. Where the analyte and background absorb at non-overlapping wavelengths the analyte spots present as dark spots against a fluorescent background. Moreover, the darkness of the spot is directly related to the amount of analyte present and therefore is relatable to analyte concentration in the original sample. Light sources suitable for such embodiments may emit advantageously around 254 nm, and since all of the emission is attributable to the background emission field no filter optics are necessary. The detector can comprise any image-forming detector such as a dedicated CCD, or an off-the-shelf cell phone or digital camera. The skilled artisan will appreciate that these detectors are merely exemplary and not limiting. Optical detection hardware within the scope of the invention includes cell phone cameras such as the Samsung-SM-G930V, CCD cameras such as TRAX UV™, and CMOS (complementary metal-oxide semiconductor) sensors any or all of which may be integrated with an imaging chamber that may exclude ambient light and may also include structures for supporting optical components in an optically aligned relation relative to each other and/or the sample.

Figure 5:
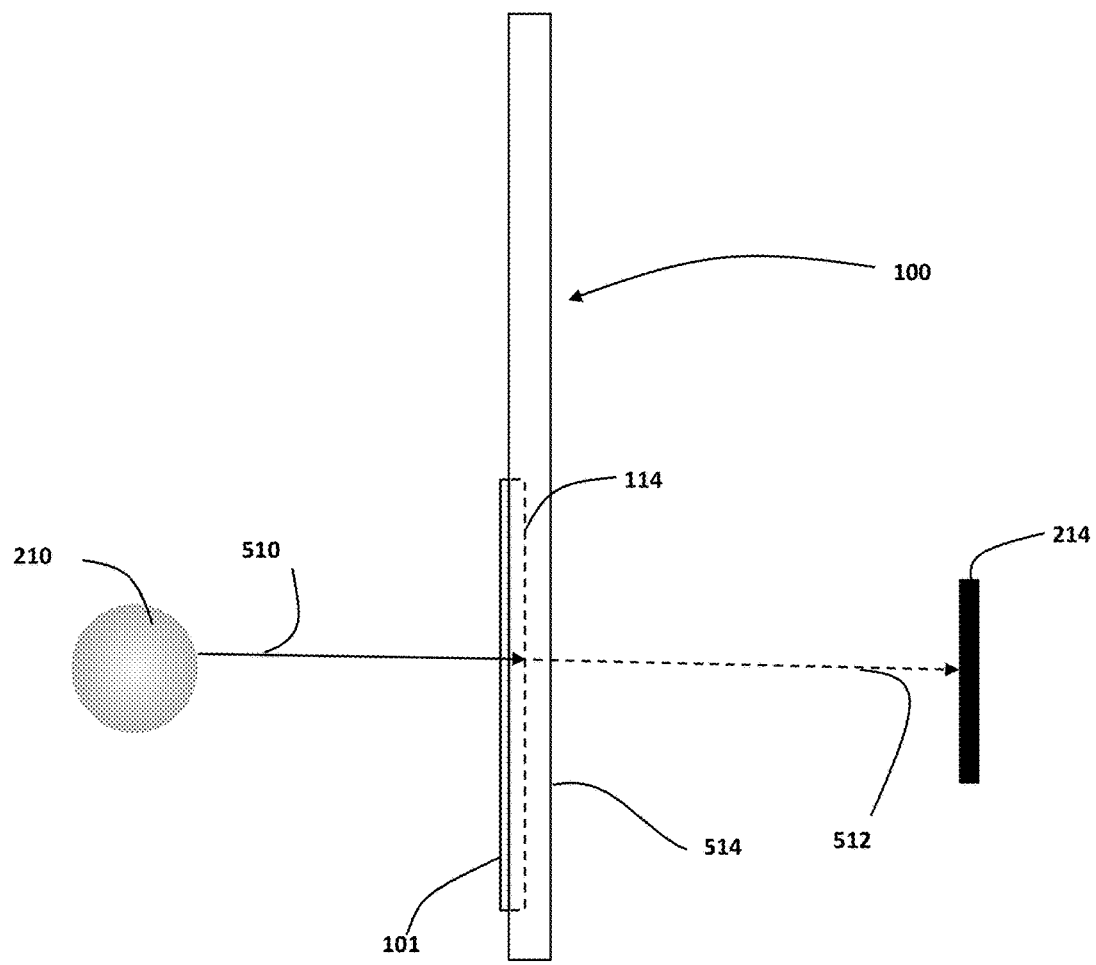
FIG. 5 illustrates a transmission mode embodiment.

FIG. 5 illustrates a transmission mode embodiment. An embodiment cartridge 100 is shown interposed between a light source 210 and a detector 214. Excitation ray 510 is illustrated with a solid arrow being emitted from the source 210 and transmitting through an optically clear sample cover 101. Excitation ray 510 is incident upon a stationary phase 114 and possibly a sample. An emission ray is illustrated by dashed line 512 being emitted either from the stationary phase 114 as in embodiments operating according background emission field methods, or from a sample as in embodiments operating according to native or enhanced fluorescence methods. A long pass optical filter 514 is shown integrated into the back panel of the cartridge 100 to filter out excitation ray 510, while passing emission ray 512.

Imaging

Processing and quantitation of sample images may be carried out according to similar algorithms for both color (e.g. RGB) and monochrome images. In either case an image stacking procedure may be used whereby multiple images are averaged together to improve signal-to-noise ratio.

Figure 6:
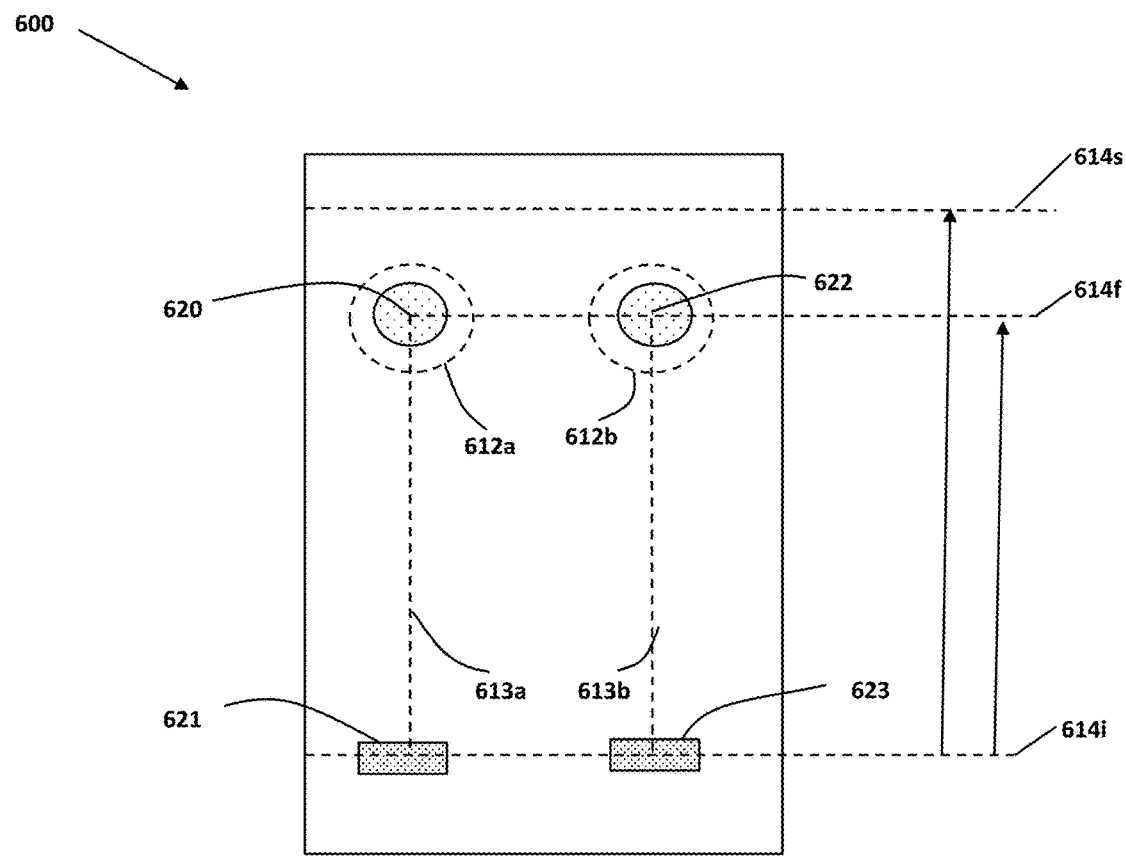
FIG. 6 illustrates an embodiment TLC plate with marks showing imaging landmarks.

Each image includes one standard spot 621 of 1 mg/mL THC (or other cannabinoid) and one unknown sample spot 623 to be analyzed in a grid as shown in FIG. 6. The plate 600 is analyzed by drawing a horizontal line 614$i$ marking the initial position of the sample 623 and standard spots 621. The ordinarily skilled artisan will readily appreciate that such lines and other markings described herein need not be literally drawn, but rather may be logically inferred especially in instrumental analysis. A mobile phase carries the standard along path 613$a$ and the sample components along 613$b$. The centroid of the THC standard 620 is located, and a horizontal line 614$f$ is drawn through the standard centroid 620. Any THC contained in the sample spot 623 will have a centroid 622 coinciding with that of the THC standard 620. The skilled artisan will readily appreciate that other components of the sample will have centroids at other locations along path 613$b$. An analysis area 612$a$ for the THC standard spot is generated by using a predetermined threshold value for pixel intensity, a similar analysis area 612$b$ is generated for the unknown sample. Three separate background readings are taken just outside of the analysis regions 612$a$, 612$b$ around the samples 620, 622. The fluorescence due to analyte in the unknown sample is calculated according to the basic background substation formula: $I_{analyte} = I_{integrated\ density} - [(\text{Analysis Area}) \times (I_{background})]$. A similar value $I_{standard}$ for the standard may also be calculated according to the same method.

This intensity value is then compared to calibration curves for cannabinoids to obtain the concentration of the unknown sample. Thresholding and subtraction of background fluorescence may correct for non-uniform illumination and variations between individual analytical devices and plates. The use of cannabinoid standards along with the retardation factor ($R_f$) value provide positive identification of the cannabinoid. This allows analysis of spot intensity on the sub-visual level, meaning that intensity that is too low for visual inspection can be detected by the image processing algorithm. As used herein $R_f$ is defined as distance traveled by sample 614$f$ divided by distance traveled by solvent 614$s$.

Certain analytical metrics may be used to validate embodiments of the invention including an embodiment's ability to chromatographically separate THC from interferents, its ability to identify and quantify THC in unknown samples of body fluids such as oral fluid, as well as the accuracy, precision, linearity, specificity for THC, limits of detection, limits of quantitation, and range of measurement.

Calibration curves may be generated according to known methods to relate fluorescent intensity to THC analyte concentration. Calibration solutions may be prepared at 0-500 μg/mL to establish the linear range. Quality control samples may be prepared from a different lot of certified reference standards and verified by GC-MS. All testing is done in triplicate at each concentration level. Calibration data may be subjected to a linear regression analysis to obtain a calibration curve and a linear correlation coefficient ($R^2$).

The range of measurements that an embodiment may reliably and accurately obtain may be defined as the range of measurements that produce a linear response within a predefined acceptable limit of accuracy and/or precision. Devices suitable for detecting intoxication in human subjects may have a range encompassing legally defined intoxication levels. For instance, and without limitation, a range of approximately 2 ng/mL to 500 μg/mL would be suitable.

Specificity of an embodiment may be established by comparing test results of adulterated samples having common impurities as well as known levels of THC, and THC concentration standards. Impurities may include, for instance, tobacco, alcohol, food products, and non-psychoactive cannabinoids such as CBD, CBN, and/or 11-nor-9-carboxy-θ9-THC. Embodiments reliably identify THC by its HPTLC $R_f$ value. Visualization and quantitation of sample and standard spots may be accomplished according to several different methods including by native fluorescence, enhanced fluorescence as previously described herein, as well as densitometric methods. Embodiments relying on densitometry for quantitation may derivatize the analyte so as cause it to absorb in the visible spectral range. For instance and without limitation, aqueous solutions of 0.1% 4-Benzoylamino-2,5-dimethoxyaniline, Azoic Diazo No. 24 (CAS Number 6268-05-9) is one such derivatizing agent.

The Limit of Detection (LOD) is the smallest amount of THC that can be detected. This quantity may be established for an embodiment using the standard deviation of the fluorescence intensity response and the slope of the calibration curve according to equation 1, where σ is the standard deviation of the fluorescence intensity response and m is the slope of the calibration curve.

$$LOD = \frac{3.3\sigma}{m} \quad \text{Equation (1)}$$

Limit of Quantitation (LOQ) is the smallest amount of THC that can be quantitatively measured. This quantity may be established for an embodiment using the standard deviation of the fluorescence intensity response and the slope of the calibration curve according to equation 2, where σ is the standard deviation of the fluorescence intensity response and m is the slope of the calibration curve.

$$LOD = \frac{10\sigma}{m} \quad \text{Equation (2)}$$

The reliability of embodiments may be referred to as robustness. This depends on factors that may vary significantly during real world use of an embodiment such as pH, temperature, and viscosity of the test sample; ambient temperature, ambient light, and the storage temperature of the cartridge of an embodiment and/or the reader of an embodiment.

Validation methods described herein may be consistent with the ICH Harmonized Tripartite Guideline (1996/2005). The guideline was formulated for use in the validation of analytical procedures for the identification and quantitation of the active moiety in samples containing a drug substance (among other procedures). This document was prepared to establish common characteristics to be used during validation of analytical procedures to bridge the differences found in regulations of different countries. This has been proposed by the European Union, Japan and the USA. It closely follows the requirements established by the Food and Drug Administration (FDA) for bioanalytical method validation.

It will be apparent to those skilled in the art that the above methods and apparatuses may be changed or modified without departing from the general scope of the invention. The invention is intended to include all such modifications and alterations insofar as they come within the scope of the appended claims or the equivalents thereof.

I claim:
1. An analytical cartridge, comprising:
  a sample receptacle adapted to receive a volume of liquid sample;
  a pump having an intake in fluid communication with the sample receptacle;
  a development chamber adapted to contain a thin layer chromatography mobile phase;
  a stationary phase disposed within the development chamber and suitable for conducting thin layer chromatography;
  a sample deposit area of the stationary phase in fluid communication with an output of the pump;
  a mobile phase reservoir adapted to contain a thin layer chromatography mobile phase; and
  a casing combining, into the form of a cartridge, the sample receptacle, the pump, the development chamber, the stationary phase, the sample deposit area, and the mobile phase reservoir.
2. The cartridge of claim 1, wherein the sample receptacle includes a mixer adapted to mix liquid samples contained therein.
3. The cartridge of claim 1, further comprising a cover for enclosing the development chamber.
4. The cartridge of claim 3, wherein the cover is retractable, removable, and/or optically clear to light between 190 nm and 800 nm.
5. The cartridge of claim 1, wherein the pump is a peristaltic pump.
6. The cartridge of claim 1, wherein the stationary phase, or an additive thereto, fluoresces in ultraviolet light.
7. The cartridge of claim 1, wherein the mobile phase reservoir comprises a blister pack that is breakable to communicate mobile phase contained therein to the development chamber.
8. The cartridge of claim 1 further comprising a reagent reservoir in fluid communication with a mixing chamber and/or the development chamber.
9. The cartridge of claim 8, wherein the reagent reservoir is adapted to dispense a solvent, a buffer, a derivatizing agent, and/or an emission enhancing agent to the mixing chamber and/or the development chamber.
10. A cannabinoid quantitation device, comprising:
  a cartridge according to claim 1;
  an excitation source emitting light suitable for measurably exciting electrons in a cannabinoid UV absorption band, the excitation source being in optical communication with a stationary phase of the cartridge;

an emission detection component operatively sensitive to cannabinoid emission resulting from relaxation of the excited electrons, the emission detection component being in optical communication with the stationary phase of the cartridge; and a microprocessor adapted to receive spectral data collected by the emission detection component and calculate a cannabinoid concentration from predefined calibration curves.

11. The cannabinoid quantitation device of claim 10, wherein the excitation source comprises an ultraviolet light emitting diode having operably sufficient spectral output between 210 nm and 250 nm to quantitate the cannabinoid.

12. The cannabinoid quantitation device of claim 11, wherein the excitation source simultaneously illuminates all analyte spots on the stationary phase.

13. The cannabinoid quantitation device of claim 10, wherein the emission detection component is an image-forming device operably sensitive to light between 295 nm and 315 nm to quantitate the cannabinoid.

14. The cannabinoid quantitation device of claim 13, wherein light impinging the emission detection component is filtered to exclude light from the excitation source and pass light emitted by analytes.

15. The cannabinoid quantitation device of claim 10, wherein the excitation source serially illuminates analyte spots.

16. The cannabinoid quantitation device of claim 15, wherein the excitation source comprises an ultraviolet LED laser having operably sufficient spectral output between 210 nm and 250 nm to quantitate the cannabinoid.

17. The cannabinoid quantitation device of claim 15, wherein the excitation source comprises a non-laser collimated ultraviolet LED having operably sufficient spectral output between 210 nm and 250 nm to quantitate the cannabinoid.

18. The cannabinoid quantitation device of claim 15, further comprising a moveable mask adapted to expose analyte spots serially to light from a non-laser un-collimated ultraviolet LED having operably sufficient spectral output between 210 nm and 250 nm to quantitate the cannabinoid.

19. The cannabinoid quantitation device of claim 15, wherein the emission detection component is a non-image-forming device operably sensitive to light between 295 nm and 315 nm to quantitate the cannabinoid.

20. The cannabinoid quantitation device of claim 10 further comprising an imaging chamber adapted to exclude ambient light and adapted to support the cartridge, the excitation source, the emission detection component, and the microprocessor in an optically aligned relation to each other.

* * * * *